(12) United States Patent
Graziani et al.

(10) Patent No.: US 7,745,457 B2
(45) Date of Patent: Jun. 29, 2010

(54) MERIDAMYCIN ANALOGUES FOR THE TREATMENT OF NEURODEGENERATIVE DISORDERS

(75) Inventors: Edmund Idris Graziani, Chestnut Ridge, NY (US); Kevin Pong, Robbinsville, NJ (US)

(73) Assignee: Wyeth LLC, Madison, NJ (US)

( * ) Notice: Subject to any disclaimer, the term of this patent is extended or adjusted under 35 U.S.C. 154(b) by 343 days.

(21) Appl. No.: 11/713,972

(22) Filed: Mar. 5, 2007

(65) Prior Publication Data

US 2007/0213525 A1 Sep. 13, 2007

Related U.S. Application Data

(60) Provisional application No. 60/779,940, filed on Mar. 7, 2006.

(51) Int. Cl.
*C07D 498/18* (2006.01)
*C07D 498/22* (2006.01)
*A61K 31/436* (2006.01)

(52) U.S. Cl. .................. 514/291; 514/411; 540/456
(58) Field of Classification Search ............. 540/456; 514/291, 411
See application file for complete search history.

(56) References Cited

U.S. PATENT DOCUMENTS

| 7,247,650 B2 | 7/2007 | Summers |
| 2005/0197356 A1 | 9/2005 | Graziani et al. |
| 2005/0197379 A1 | 9/2005 | Summers et al. |
| 2005/0272133 A1 | 12/2005 | He et al. |
| 2006/0135549 A1 | 6/2006 | Graziani et al. |
| 2006/0135550 A1 | 6/2006 | Graziani et al. |
| 2006/0141583 A1 | 6/2006 | Haltli |

FOREIGN PATENT DOCUMENTS

| WO | WO 94/18207 A1 | 8/1994 |
| WO | WO 95/06649 | 3/1995 |
| WO | WO 95/14023 A | 5/1995 |
| WO | WO 2005/084673 A1 | 9/2005 |
| WO | WO 2005/085257 A1 | 9/2005 |
| WO | WO 2005/121327 A2 | 12/2005 |
| WO | WO 2006/068905 A3 | 6/2006 |
| WO | WO 2006/068932 A2 | 6/2006 |

OTHER PUBLICATIONS

Testa, Prodrugs Revisited: The "Ad Hoc" Approach as a Complement to Ligand Design, Medicinal Research Reviews, 16(3):233-241, (1996).
Salituro et al, Meridamycin: A Novel Nonimmunosuppressive FKBP12 Ligand From *Streptomyces hygroscopicus*, Tetrahedron Letters, vol. 36, No. 7, pp. 997-1000, (1995).
Summers et al, 3-Normeridamycin: A Potent Non-Immunosuppressive Immunophilin Ligand is Neuroprotective in Dopaminergic Neurons, J. Antibiot. 59(3):184-189, (Mar. 2006).
H. Lin et al; Correlation Between Hippocampal Mossy Fiber Sprouting and Synaptic Reorganization and Mechanisms of Temporal Lobe Epilepsy; Zhonghua Yi Xue Za Zhi; vol. 87(5) pp. 341-344; 2007.
L. A. Shapiro et al; Integration of Newly Born Dentate Granule Cells Into Adult Brains; Hypotheses Based on Normal and Epileptic Rodents; Brain Res Brain Res Rev; vol. 48(1); pp. 43-56; 2005.
A. Knopp et al; Cellular and Network Properties of the Subiculum in the Pilocarpine Model of Termporal Lobe Epilepsy; j Comp Neurol; vol. 483(4); Pgsl; 475-488; 2005.
C. E. Bandtlow et al; Increased Expression of Nogo-A in Hippompl Neurons of Patients With Temporal Lobe Epilepsy; Eur J. Neurosci; vol. 20(1); pp. 195-206; 2004.
X. Bao et al; Brain Dev; Alpers Syndrome With Prominent WHIT4E Matter Changes vol. 30(4; 2008(4) 2008.
A. Simonati et al.; Features of Cell Death in Brain and Liver, The Target Tissues of Progressive Neuronal Degeneration of Childhood With Liver Disease (Alphers-Huttennlocher Disease); Acta Neuropathol; vol. 106(1); pp. 57-65; 2003.
S. Ulmer et al; Detectionof Acute Cytotoxic Changes in Progressive Neuronal Degenerationof Childhood With Liever Disease (Alpers-Huttenlocher Syndrome) Using Diffusion-Weighted MRI and MR Spectorscopy; J. Comput Assist Tomogr; vol. 26(4); pp. 641-656; 2002.
J. E. Kang et al; Regulationof the Proapoptotic Acitivty of Huntingtin Interacting Protein 1 by DYRK1 and Caspases-3 in Hippodampail Neuroprogenitor Cells; J. Neurosci Res; vol. 81(1); pp. 62-72; 2005.
G. Douaud et al; In Vivo Evidence for the Selective Subcortical Degeneration in Huntington'S Disease; Neuroimage; vol. 46(4); pp. 958-966; 2009.
P. R. Joshi et al; Age-Dependent Alterations of Corticostriatal Activity in the YAC128 Mouse Model of Huntington Disease; J. Neurosci; vol. 29(8); pp. 2414-2427; 2009.

(Continued)

*Primary Examiner*—Bruck Kifle
(74) *Attorney, Agent, or Firm*—Michael J. Herman

(57) ABSTRACT

A compound of the structure

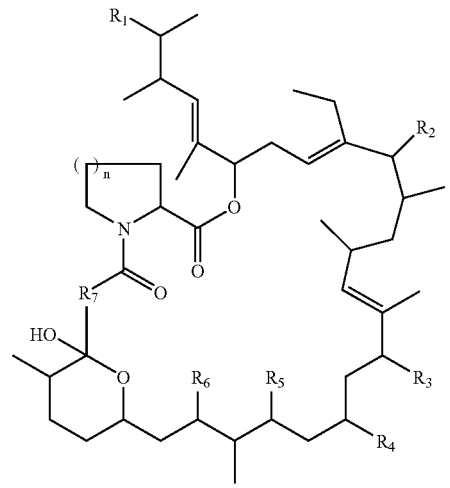

is described. This compound and its use for preparing medicines useful in the treatment of neurodegenerative disorders is described.

29 Claims, No Drawings

OTHER PUBLICATIONS

J. Spampanato et al.; Progressive Synaptic Pathology of Motor Cortical Neurons in a BAC Transgenic Mouse Model of Huntington'S Disease; Neuroscience; vol. 157(3); pp. 606-620; 2008.

A. Thompson et al; Changes in Adult Neurogenesis in Neurodegenerative Diseases; Cause or Consequence?; Genes Brain Behav.; Suppl 1; pp. 28-42; 2008.

A.E. Metz et al; Morphological and Functional Reorganization of Rat Medial Prefrontal Cortex in Neuropathic Pain; Proc. Natl Acad Sci USA; vol. 106(7) pp. 2423-2428; 2009.

Y. S. Kim et al; Protective Effect of Gabapentin on N-Methyl-D-Aspartate-Induced Excitotoxicity in Rat Hippocampal CA1 Neurons; J. Pharmacol Sci; vol. 109(1); pp. 144-147; 2009.

P. V. Belichenko et al; Widespread Changes in Dendritic and Axonal Morphology in MECP2-Mutant Mouse Models of Rett Syndrome; Evidence for Disruption of Neuronal Networks; J. Comp Neurol; vol. 514(3) pp. 240-258; 2009.

M. Fischer et al; Enhanced Hupoxia Susceptibility in Hippocampal Slices Froma Mouse Model of Rett Syndrome; J. Neurophysio; vol. 101(2); pp. 1016-1032; 2009.

R. D. Smrt et al; MECP2 Deficiency Leads to Delayed Maturation and Altered Gene Expresion in Hippocampai Neurons; Neurobio Dis.; vol. 27(1); pp. 77-89; 2007.

V. S. Dani et al; Reduced Cortical Activity Due to a Shift in the Balance Between Excitation and Inhibiton ina Mouse Model of Rett Syndrome; Proc Natl Acad Sci USA; vol. 102(35); pp. 12560-12565; 2005.

P. Filipcik et al; Corticall and Hippocampl Neurons From Truncated Tau Transgenic Rat Express Multiple Lmarkers of Neurodegeneration; Cell Mol Neurobiol; 2009.

J B Melo et al; Galantamine Protects Against Oxidative Stress Induced by Amyuloid-Beta Peptide in Cortical Neurons; Eur J. Neurosci; vol. 29(3); pp. 455-464; 2009.

B. Malik et al; Cell Cycle-Drive Neuronal Apoptosis Specficially Linked to Anmyloid Peptide ABeta1-42 Exposure is not Exacertated in a Mouse Model of Presenliin-1 Familial Alzheimer's Disease; J. Neurochem; vol. 106(2); pp. 912-916; 2008.

A Rametti et al; Lithium Down-Regulates Tau in Cultured Cortical Neurons; A Possible Mechanism of Neuroprotection; Neurosci Lett; vol. 434(1); pp. 93-98; 2008.

M N Vieira et al; Soluble Oligomers From a Non-Disease Related Protein Mimic ABeta-Induced Tau Hyperphosphorylation and Neurodegeneration; J. Neurochem; vol. 103(2); pp. 736-748; 2007.

M Hu et al; High Content Screen Microscopy Analysis of a Beta 1-42 Induced Neurite Outgrowth Reduction in Rat Primary Cortical Neurons; Neuroprotective Effects of Alpha 7 Neuronal Nicotinic Acetylcholine Receptor Ligands; Brain Res.; vol. 1151; pp. 227-235; 2007.

H Oakley et al; Intraneuronal Beta-Amyloid Aggregates, Neurodegeneration, D Neuron Loss in Transgenic Mice With Five Famlal Alzheimer's Disease Mutations; Potential Factors in Amyloid Plaque Formatin; J. Neurosci; vol. 26(40); pp. 10129-10140; 2006.

C. Culmsee et al; Molecular Insights Into Mechanisms of the Cell Death Program: Role in the Progression of Neurodegenerative Disorders; Curr Alzheimer Res.; vol. 3(4); pp. 269-283; 2006.

G E Hoffman et al; Neuroprotection by Ovarian Hormones in Animal Models of Neurological Disease; Endocrine; vol. 29(2); pp. 217-231; 2006.

I. Merchanthaler et al; Neuroprotection by Estrogen in Animal Models of Global and Focal Ischemia; Ann N Y Acad Sci; vol. 1007; pp. 89-100; 2003.

W C Shuy et al; Secretoneurin Promotes Neuorportection and Neuronal Plasticity Via the JAK2/STAT3 Pathway in Murine Models of Stroke; J. Clin Invest; vol. 118(1); pp. 133-148; 2008.

C Wiessner et al; Anti-Nogo-A Antibody Infusion 24 Hours After Experimaental Stroke Improved Behavioral Outcome and Corticospinal Plasticity in Normotensive and Spontaneously Hypertensive Rats; J. Cereb Blood Flow Metab; vol. 23(2); pp. 154-165; 2003.

R. Dutta et al; Activation of the Cililary Neurotrophic Factor (CNTF) Signalling Pathway in Cortical Neurons of Multiple Sclerosis Patients; Brain; vol. 130(Pt 10) pp. 2566-2576; 2007.

P N Koutsoudaki et al; Demyelination of the Hippocampus is Prominent in the Cuprizone Model; Neurosci lett; vol. 451(1); pp. 83-88; 2009.

J J Geurts et al; Grey Matter Pathology in Multiple Sclerosis; Lancet Neurol; vol. 7(9); pp. 841-851; 2008.

D K Cullen et al; Collagen-Dependent Neurite Outgrowth and Response to Dynamic Deformation in Three-Dimensional Neuronal Cultures; Ann Biomed Eng; vol. 35(5); pp. 835-846; 2007.

P M Lenzlinger et al; Delayed Inhibition of Nogo-A Does Not Alter Injury0induced Axonal Sprouting but Enhances Recovery of Cognitive Function Following Experimental Traumatic Brain Injury in Rats; Neuroscience; vol. 134(3); pp. 1047-1056; 2005.

M J Jurynec et al; TIGR is Upregulated in the Chronci Glial Scar in Response to Cnetral Nervous System Injury and Inhibits Neurite Outgrowth; Mol Cell Neurosci; vol. 23(1); pp. 69-80; 2003.

JJ Ramirez et al; Basic Fibroblast Growth Factor Enchances Axonall Srpouting After Cortical Injury in Rats; Neuroreport; vol. 10(6); pp. 1201-1204; 1999.

H Peng et al; Epidermal Growth Factor Protects Neuronal Cells in Vivo and in Vivo Against Transient Foreberain Ischemia-and Free Radical-Induced Injuries; J Cereb Blood Flow Metab; vol. 18(4); pp. 349-360; 1998.

J S Rudge et al; Inhibition of Neurite Outgrowth on Astroglial Scars in Vitro; J. Neurosci; vol. 10(11); pp. 3594-3603; 1990.

W L Kuan et al; Increased Capacity for Axonal Outgrowth Using Xenogenic Tissue in Vitro and in a Rodent Model of Parkinson's Disease; Xenotransplantation; vol. 13(3); pp. 233-247; 2006.

Y Li et al; GLP-1 Receptor Stimulation Preserves Primary Cortical and Dopaminergic Neurons in Cellular and Rodent Models of Stroke and Parkinsonism; Proc Natl Acad Sci USA; vol. 106(4); pp. 1285-1290; 2009.

E Kyratzi et al; The S18Y Polymorphic Variant of UCH-L1 Confers an Antioxidant Function to Neuronal Cells; Hum Mol Genet; vol. 17(14); pp. 2160-2170; 2008.

M Hashimoto et al; Beta-Synuclein Regulates AKT Activity in Neuronal Cells. A Possible Mechanism for Neuroprotection in Parkinson's Disease; J. Biol Chem; vol. 279(22); pp. 23622-23629; 2004.

Y Wang et al; Diadenosine Tetraphosphate Protects Agains Injuries Induced by Ischemia and 6-Hydroxydopamine in Rat Brain; J. Neurosci; vol. 23(21); pp. 7958-7965; 2003.

T K Murray et al; LY503430, An Oval Alpha-Amino-3-Hydroxy-5-Methylisoxazole-4-Propionic Acid Receptor Potentiator With Functional, Neuroprotective and Neurotorphic Effects in Rodent Models of Parkinson's Disease; J Pharmacol Exp Ther; vol. 306(2); pp. 752-762; 2003.

T Suuronen et al; Protective Effect of L-Deprenyl Against Apoptosis Induced by Okadaic Acid in Cultrued Neuronal Cells; Biochem Pharmacol; vol. 59(12); pp. 1589-1595; 2000.

E S Lee et al; Estrogen and Tamoxifen Protect Agains MN-Induced Toxicity in Rat Cortical Primary Cultures of Neurons and Astrocytes; Toxicol Sci; vol. 110(1) pp. 156-167; 2009.

A Galvan et al; Pathophysiology of Parkinsonism; Clin Neurophysiol; vol. 119(7); pp. 1459-1474; 2008.

C Lai et al; Amyotrophic Lateral Sclerosis 2-Deficiency Lead to Neuronal Degeneration in Amyotrophic Lateral Sclerosis Through Altered AMPA Receptor Trafficking; J Neurosci; vol. 26(45); pp. 11798-11806; 2006.

M Azzouz et al; Increased Motoneuron Survival and Improved Neuromuscular Funciton in Transgenic ALS Mice After Intraspinal Injection Adeno-Associated Virus Encodeing BCL-2; Hum Mol Genet; vol. 9(5); pp. 803-811; 2000.

V N Trieu et al; Genistein is Neuroprotective in Murine Models of Familial Amyotrophic Lateral Sclerosis and Stroke; Biochem Biophys Res Commun; vol. 258(3); pp. 685-688; 1999.

S Kalra et al; Recovery of N-Acetylaspartate in Corticomotor Neurons of Patients With ALS After Filuzole Therapy; Neuroreport; vol. 9(8); pp. 1757-1761; 1998.

D L Price et al; Dysfunction and Death of Neurons in Human Degenerative Neurological Diseases and in Animal Models; Ciba Found Symp; vol. 126; pp. 30-48; 1987.

MERIDAMYCIN ANALOGUES FOR THE TREATMENT OF NEURODEGENERATIVE DISORDERS

CROSS-REFERENCE TO RELATED APPLICATION

This application claims the benefit under 35 USC 119(e) of U.S. Provisional Patent Application No. 60/779,940, filed Mar. 7, 2006.

BACKGROUND OF THE INVENTION

This invention relates to meridamycin compounds, methods of preparation, and methods of use thereof.

Meridamycin has been identified for uses such as an antidote for an overdose of macrophilin-binding-immunosuppressants such as FK506 or rapamycin, a steroid potentiator, and/or an anti-infective agent for infections or infectious diseases caused by organisms producing MIP (macrophage infectivity potentiator) or Mip-like factors. See, International Patent Publication No. WO 94/18207. In addition, meridamycin may be useful in the treatment of inflammatory/hyperproliferative skin diseases.

Meridamycin has been isolated from a strain of *Streptomyces hydroscopicus* as described in Salituro et al., Tet. Lett, 36(7): 997-1000 (1995).

Meridamycin and derivatives thereof have been prepared as described in US Published Patent Application No. US 2005/0272133A1 (Dec. 8, 2005; U.S. patent application Ser. No. 11/143,980) and US Patent Application Publication No. US 2005-0197379-A1. Compounds derived from meridamycin (described in International Patent Publication No. WO 2005/084673) have been shown to demonstrate neuroprotective effects (see also, International Patent Publication No. WO 2005/085257 and US Patent Application Publication No. US 2005-0197379 A1.

What are needed in the art are alternate meridamycin derivatives.

SUMMARY OF THE INVENTION

In one aspect, the invention provides a compound of the structure:

In another aspect, the invention provides methods of preparing the compounds of the invention.

In still another aspect, the invention provides compositions containing the compounds of the invention.

In a further aspect, the invention provides for the use of the compounds of the invention in preparing medicaments.

In still a further aspect, the invention provides a method of treating a neurological disorder comprising administering a compound of the invention to a mammalian subject.

Other aspects and advantages of the invention will be readily apparent from the following detailed description of the invention.

DETAILED DESCRIPTION OF THE INVENTION

As described herein, the invention provides a compound of the structure:

wherein:

$R_1$ and $R_2$ are, independently selected from the group consisting of, OH, oxo, O($C_1$ to $C_6$ alkyl), O(substituted $C_1$ to $C_6$ alkyl), O(acyl), O(aryl), O(substituted aryl), or O(heterocyclyl), O(substituted heterocyclyl);

$R_3$, $R_4$, $R_5$, and $R_6$ are independently selected from the group consisting of OH, oxo, O($C_1$ to $C_6$ alkyl), O(substituted $C_1$ to $C_6$ alkyl), O(acyl), O(aryl), O(substituted aryl), O(heterocyclyl), and O(substituted heterocyclyl); or $R_3$ and $R_4$ and/or $R_4$ and $R_5$, or $R_5$ and $R_6$ are joined (taken together) to form a structure:— wherein X and Y are independently selected from the group consisting of H, $C_1$ to $C_6$ alkyl, substituted $C_1$ to $C_6$ alkyl, aryl, substituted aryl, heterocyclyl, and substituted heterocyclyl;

$R_7$ is $CH_2$, CHOH, or C=O; and n is 1 or 2;

or a pharmaceutically acceptable salt thereof.

In one embodiment, $R_1$ and $R_2$ are independently selected from among oxo, OH or O(acyl). One suitable O(acyl) is $OC(O)CH_3$. Other suitable O(acyl)s can be selected.

In another embodiment, $R_3$ and $R_4$ or $R_4$ and $R_5$ are joined, wherein X and Y are $CH_3$.

In yet another embodiment, $R_7$ is C(O).

In still another embodiment, $R_1$ and $R_2$ are OH; $R_3$ and $R_4$ are joined; $R_5$ and $R_6$ are joined; $R_7$ is C(O); and n is 2

In yet another embodiment, $R_1$, $R_2$, $R_3$, $R_4$, $R_5$, and $R_6$ are $OC(O)CH_3$; $R_7$ is C(O); and n is 2.

In another embodiment, $R_1$, $R_2$, $R_3$, and $R_4$ are $OC(O)CH_3$; $R_4$ and $R_5$ are OH; $R_7$ is C(O); and n is 2.

In still another embodiment, $R_1$, $R_2$, $R_5$, and $R_6$ are OH; $R_3$ and $R_4$ are joined; $R_7$ is C(O); and n is 2.

In a further embodiment, $R_1$, $R_2$, $R_3$, $R_4$, and $R_5$ are $OC(O)CH_3$; $R_6$ is OH; $R_7$ is C(O); and n is 2.

In another embodiment, $R_1$ and $R_2$ are oxo; $R_3$ and $R_4$ and $R_5$ and $R_6$ are joined; $R_7$ is C(O); and n is 2.

In yet another embodiment, $R_1$ and $R_2$ are oxo; $R_3$, $R_4$, $R_5$, and $R_6$ are OH; $R_7$ is C(O); and n is 2.

In a further embodiment, $R_4$ and $R_5$ are taken together to form a ring of the structure

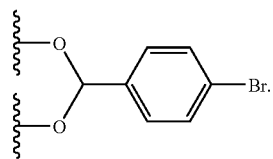

Examples of suitable compounds of the invention include:

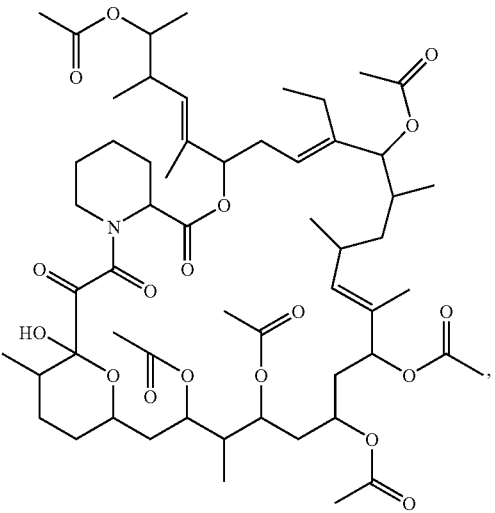

-continued

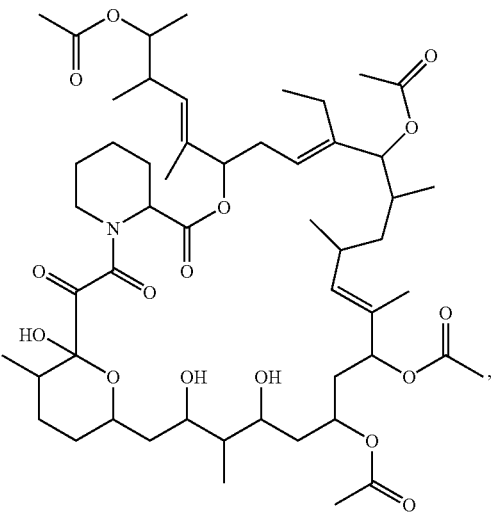

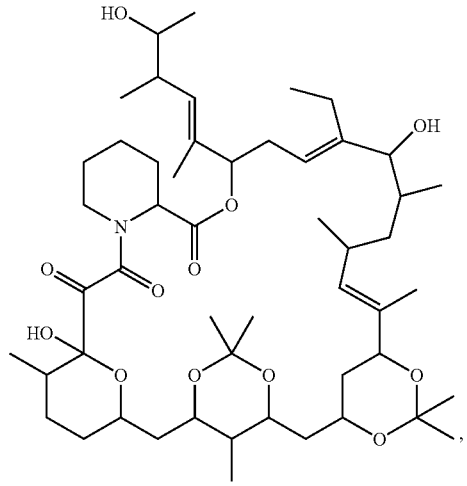

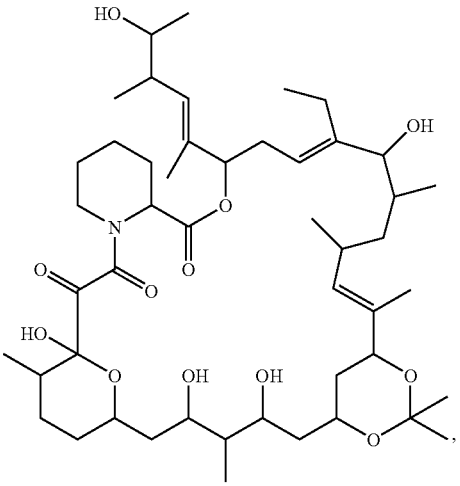

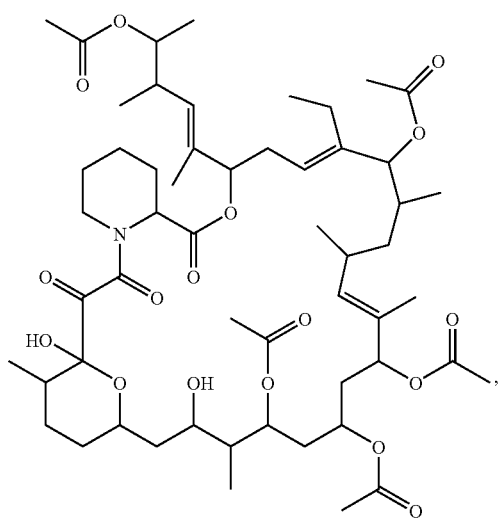

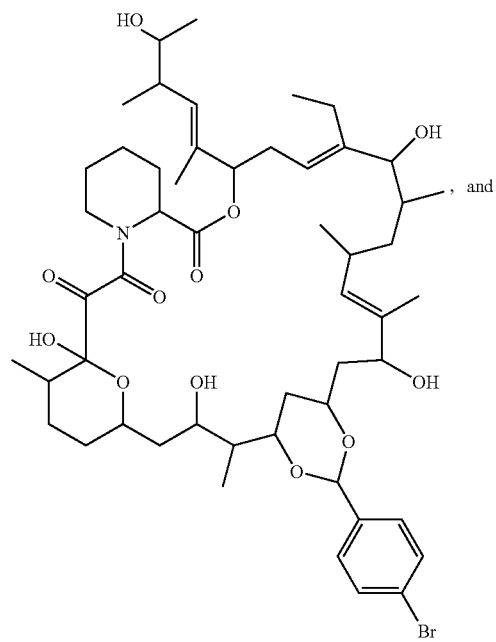

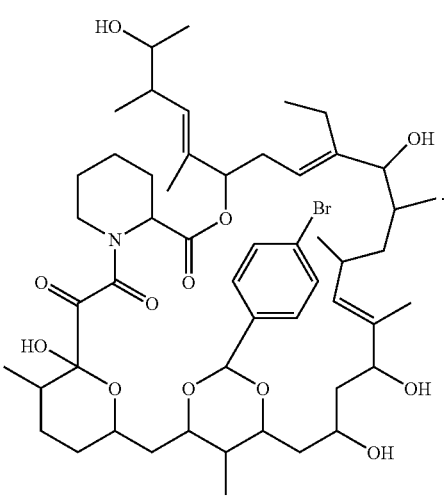

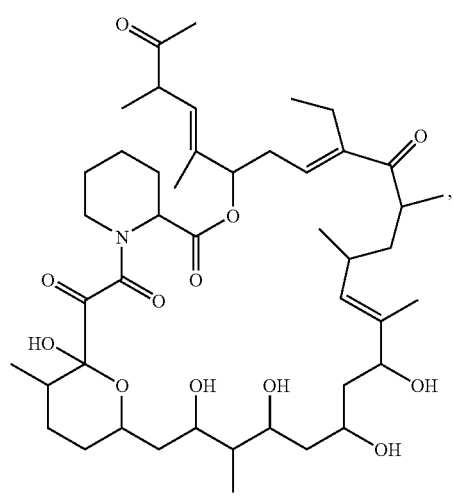

The term "alkyl" is used herein to refer to both straight- and branched-chain saturated aliphatic hydrocarbon groups having one to ten carbon atoms, desirably one to eight carbon atoms and, most desirably, one to six carbon atoms; "alkenyl" is intended to include both straight- and branched-chain alkyl group with at least one carbon-carbon double bond and two to eight carbon atoms, desirably two to six carbon atoms; "alkynyl" group is intended to cover both straight- and branched-chain alkyl groups with at least one carbon-carbon triple bond and two to eight carbon atoms, desirably two to six carbon atoms. Examples of alkyl include methyl, ethyl, n-propyl, i-propyl and n-butyl. Examples of alkenyl include ethenyl, prop-1-yl and prop-2-yl. Examples of alkynyl include ethynyl.

The terms "substituted alkyl", "substituted alkenyl", and "substituted alkynyl" refer to alkyl, alkenyl, and alkynyl groups defined above having from one to three substituents selected from halogen, CN, OH, NO$_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio. Where there is more than one substituent they may be the same or different. These substituents may be attached to any carbon of an alkyl, alkenyl, or alkynyl group provided that the attachment constitutes a stable chemical moiety.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane. The aryl is suitably a 6 to 13 carbon aryl or a 6 to 10 carbon aryl.

The term "substituted aryl" refers to aryl as defined above having one to four substituents selected from halogen, CN, OH, NO$_2$, amino, alkyl, cycloalkyl, alkenyl, alkynyl, alkoxy, aryloxy, substituted alkyloxy, alkylcarbonyl, alkylcarboxy, alkylamino, and arylthio. Where there is more than one substituent they may be the same or different.

The term "heterocyclyl" is used herein to describe a 4- to 7-membered monocyclic or a stable multicyclic heterocyclyl ring which is saturated, partially unsaturated, or unsaturated, and which includes carbon atoms and from one to four heteroatoms selected from the group including N, O, and S atoms. The N and S atoms may be oxidized. The heterocyclyl ring also includes any multicyclic ring in which any of above defined heterocyclyl rings is fused to an aryl ring. The heterocyclyl ring may be attached at any heteroatom or carbon atom provided the resultant structure is chemically stable. Such heterocyclyl groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocyclyl" is used herein to describe the heterocyclyl defined above having one to four substituents selected from halogen, CN, OH, NO$_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio and substituted arylthio. Where there is more than one substituent they may be the same or different.

The term "alkoxy" is used herein to refer to the OR group, where R is alkyl or substituted alkyl as defined above and the point of attachment is on the oxygen atom.

The term "aryloxy" is used herein to refer to the OR group, where R is aryl or substituted aryl as defined above and the point of attachment is on the oxygen atom.

The term "arylthio" is used herein to refer to the SR group, where R is aryl or substituted aryl as defined above and the point of attachment is on the sulfur atom.

The term "alkylcarbonyl" or "acyl" is used herein to refer to the RCO group, where R is alkyl or substituted alkyl as defined above and the point of attachment is on the carbon atom.

The term "alkylcarboxy" is used herein to refer to the COOR group, where R is alkyl or substituted alkyl as defined above and the point of attachment is on the carbon atom.

The term "aminoalkyl" refers to both secondary and tertiary amines wherein the alkyl or substituted alkyl groups, as defined above e.g. containing one to eight carbon atoms, which may be either the same or different and the point of attachment is on the nitrogen atom.

The term "halogen" refers to Cl, Br, F, or I.

The compounds of the present invention can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof.

These salts, as well as other compounds of the invention may be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds of the present invention can be prepared as described generally in the following schemes. These methods and variations thereof will be readily understood to one skilled in the art of organic synthesis. The compounds of the present invention can be prepared using the methods described below, together with synthetic methods known in the synthetic organic arts or variations of these methods by one skilled in the art. [See, generally, *Comprehensive Organic Synthesis*, "Selectivity, Strategy & Efficiency in Modern Organic Chemistry", ed., 1. Fleming, Pergamon Press, New York (1991); *Comprehensive Organic Chemistry*, "The Synthesis and Reactions of Organic Compounds", ed. J. F. Stoddard, Pergamon Press, New York (1979)]. Suitable methods include, but are not limited to, those outlined below.

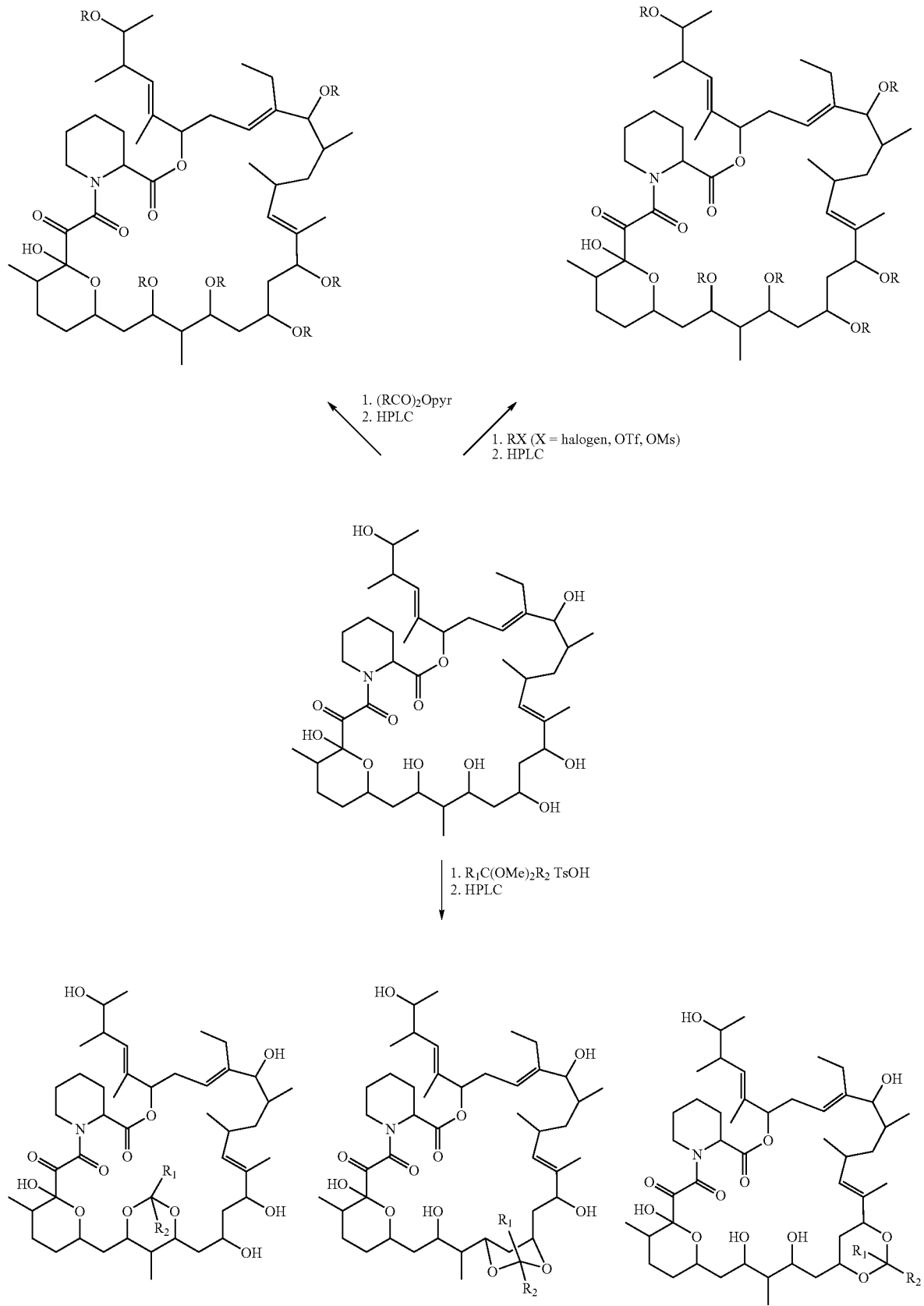

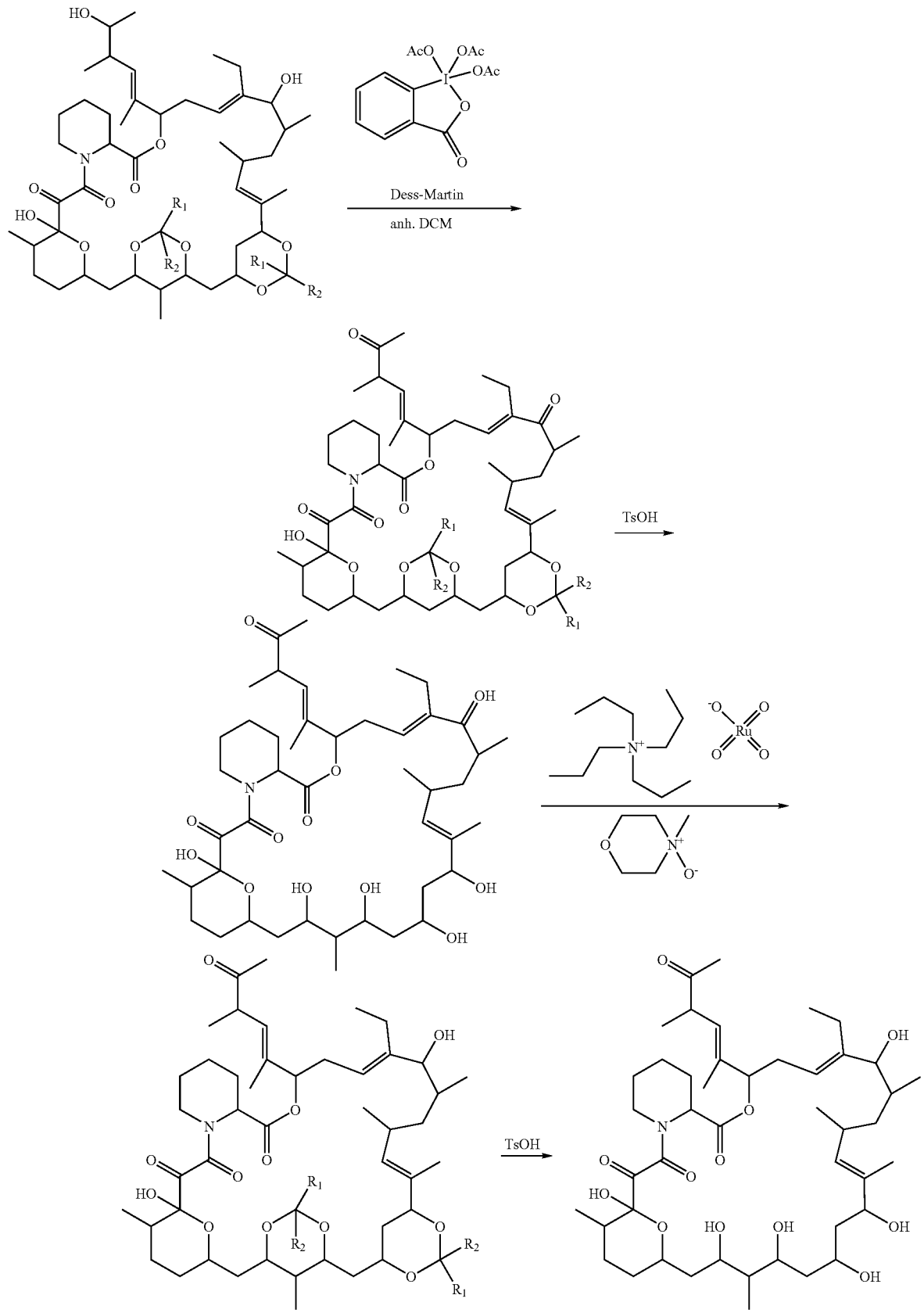

In one aspect, the invention provides a method of preparing a compound having the structure 1, wherein:

$R_1$, $R_2$, $R_3$, $R_4$, $R_5$, and $R_6$ are, independently, O($C_1$ to $C_6$ alkyl) or O(substituted $C_1$ to $C_6$ alkyl);

$R_7$ is $CH_2$, CHOH, or C=O; and n is 1 or 2;

or a pharmaceutically acceptable salt thereof. This method involves reacting meridamycin with an alkylating agent or alkyl anhydride.

Meridamycin and derivatives thereof have been prepared as described in US Published Patent Application US 2005-0272133 A1 and US Patent Application Publication No. US 2005-0197379-A1, which are hereby incorporated by reference. However, the present invention is not limited by the source of meridamycin pounds of the invention, when $R^1$ and $R^2$ are other than Oalkyl groups, an acid halide or aryl anhydride are typically utilized to obtain the compound of the invention. Typically, a mild base (e.g. pyridine) is utilized when the akylating agent is an anhydride. Alternatively, the reaction may be performed utilizing a suitable anhydride (e.g., acetic anhydride).

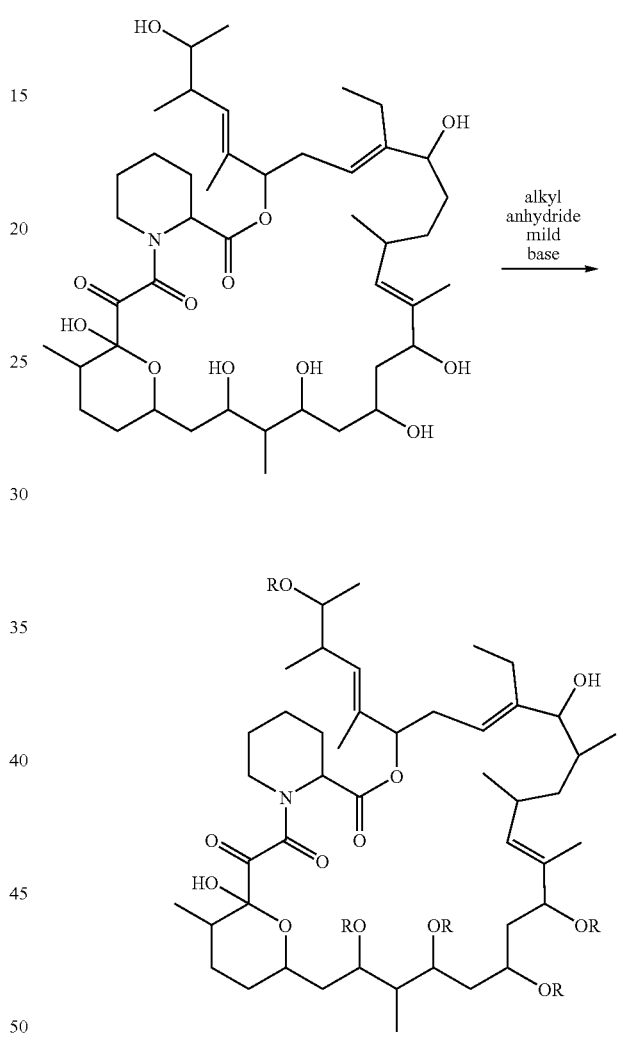

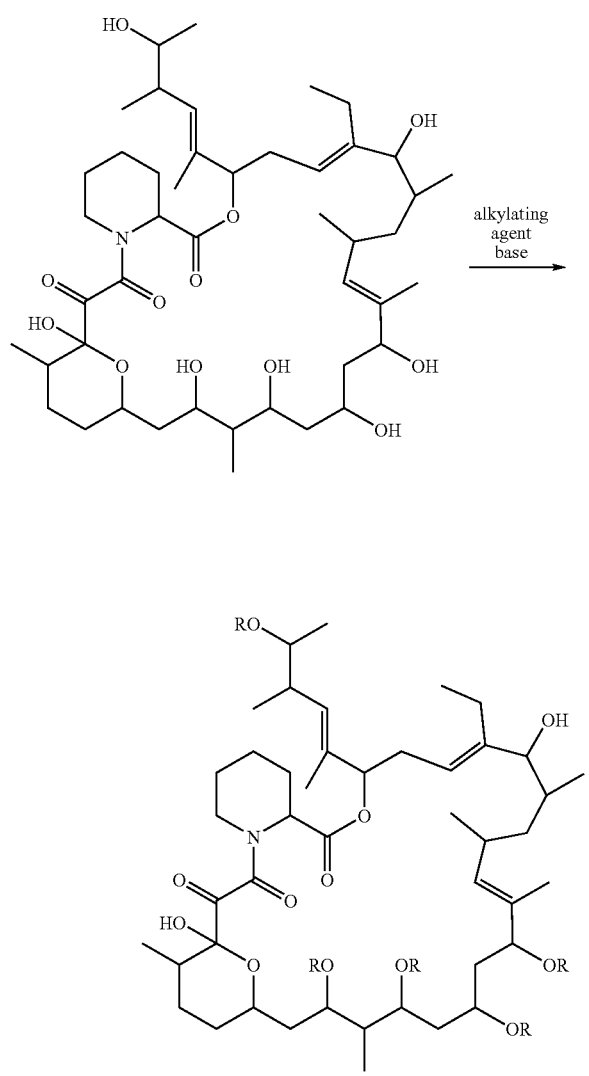

Suitable alkylating agents may be readily selected from among an alkyl halide, alkyl triflate, or alkyl mesylate. However, other suitable reagents may be substituted. For com- In another embodiment, the invention provides a method of preparing a compound of formula I, wherein $R_1$ and $R_2$ are OH; $R_3$ and $R_4$; $R_4$ and $R_5$; $R_5$ and $R_6$; or a combination thereof are joined, and Y are independently selected from the group consisting of H, $C_1$ to $C_6$ alkyl, substituted $C_1$ to $C_6$ alkyl, aryl, substituted aryl, heterocyclyl, and substituted heterocyclyle; $R_7$ is $CH_2$, CHOH, or C=O; and n is 1 or 2;

or a pharmaceutically acceptable salt thereof. This method involves reacting meridamycin with a dialkoxyalkane in the presence of an acid catalyst, e.g., TsOH, paratoluenesulfonic acid, or another mild acid. In one embodiment, the dialkoxyalkane is 2,2-dimethoxypropane.

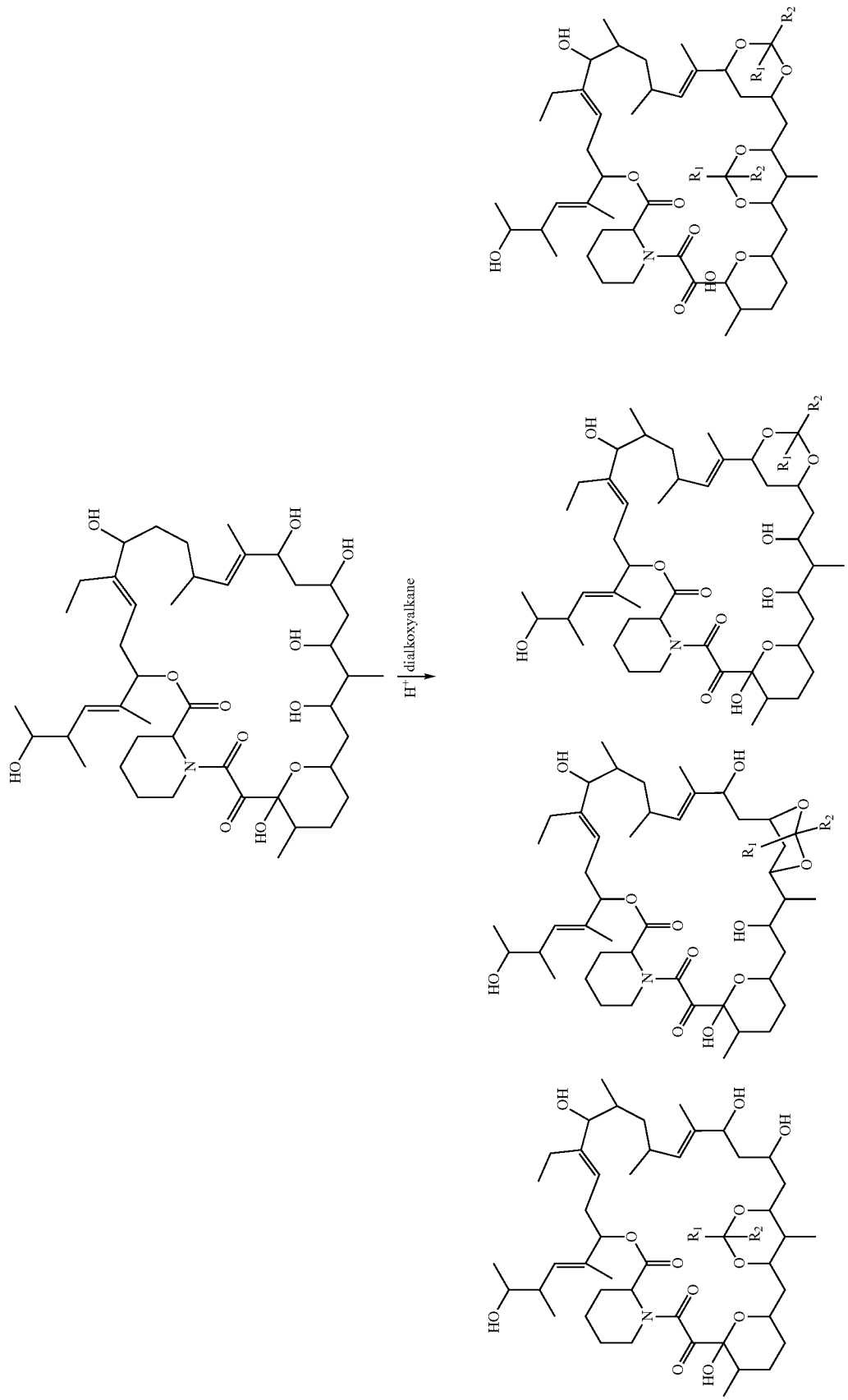

In a further embodiment, the invention provides a method of preparing a compound of the structure I: wherein $R_1$ and $R_2$ are oxo; $R_3$ and $R_4$; $R_4$ and $R_5$; $R_5$ and $R_6$; or a combination thereof are joined; X and Y are independently selected from the group consisting of H, $C_1$ to $C_6$ alkyl, substituted $C_1$ to $C_6$ alkyl, aryl, substituted aryl, heterocyclyl, and substituted heterocyclyl; $R_7$ is $CH_2$, CHOH, or C=O; and n is 1 or 2; or a pharmaceutically acceptable salt thereof. This method involves reacting a compound of structure I, wherein: $R_1$ and $R_2$ are OH; $R_3$ and $R_4$; $R_4$ and $R_5$; $R_5$ and $R_6$; or a combination thereof are joined to form a structure:—

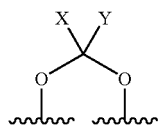

X and Y are independently selected from the group consisting of H, $C_1$ to $C_6$ alkyl, substituted $C_1$ to $C_6$ alkyl, aryl, substituted aryl, heterocyclyl, and substituted heterocyclyl;

$R_7$ is $CH_2$, CHOH, or C=O; and n is 1 or 2;

or a pharmaceutically acceptable salt thereof;

with the Dess-Martin periodinane reagent. Alternatively, the compound is reacted with tetrapropylammonium ruthenate and N-morpholine oxide In still another aspect, the invention provides a method of preparing a compound of structure 1, wherein: $R_1$ is oxo; $R_2$ is OH; $R_3$, $R_4$, $R_5$, and $R_6$ are OH; $R_7$ is $CH_2$, CHOH, or C=O; and n is 1 or 2; or a pharmaceutically acceptable salt thereof. This method involves reacting the product of the reaction with the Dess-Martin periodinane reagent (or the tetrapropylammonium ruthenate and N-morpholine oxide) with a weak acid, e.g., paratoluenesulfonic acid.

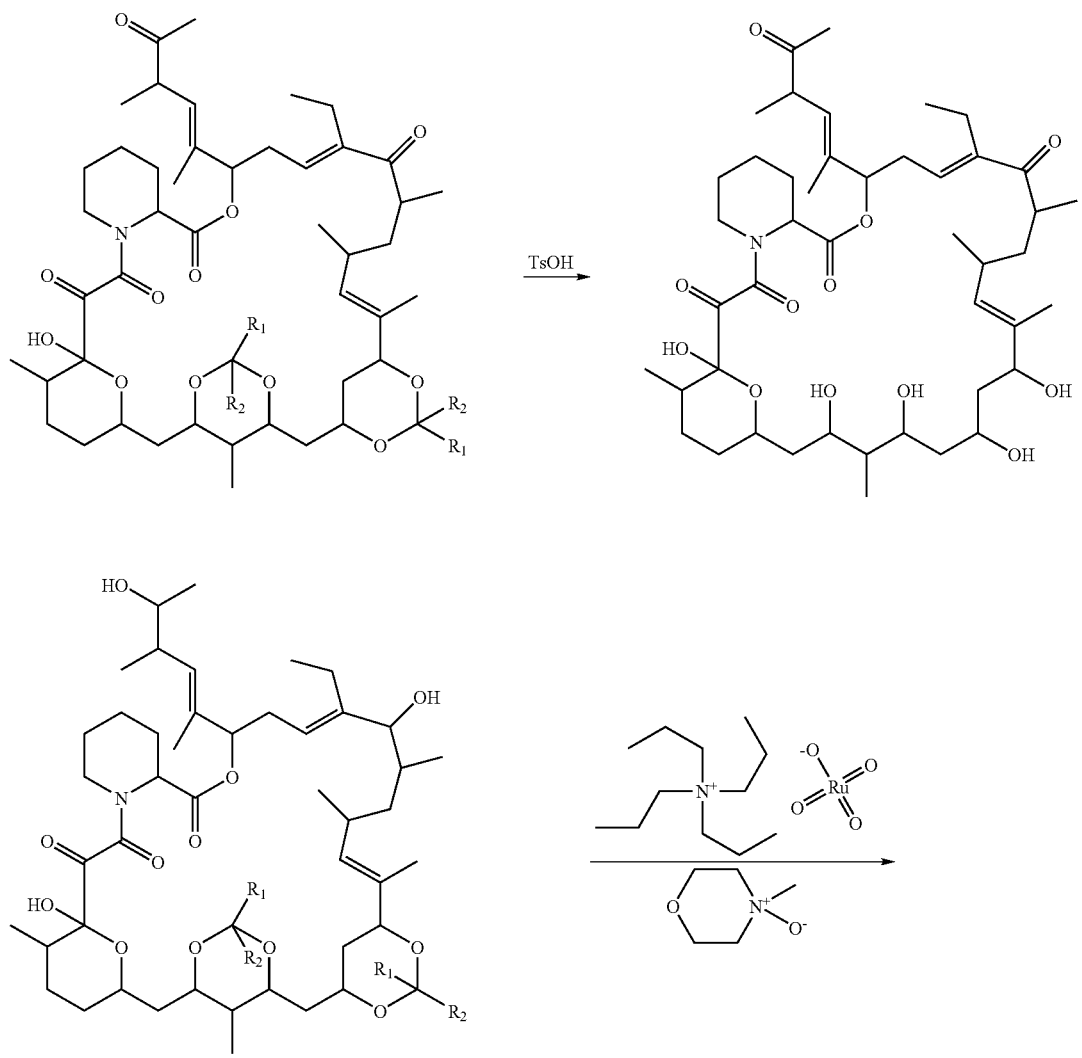

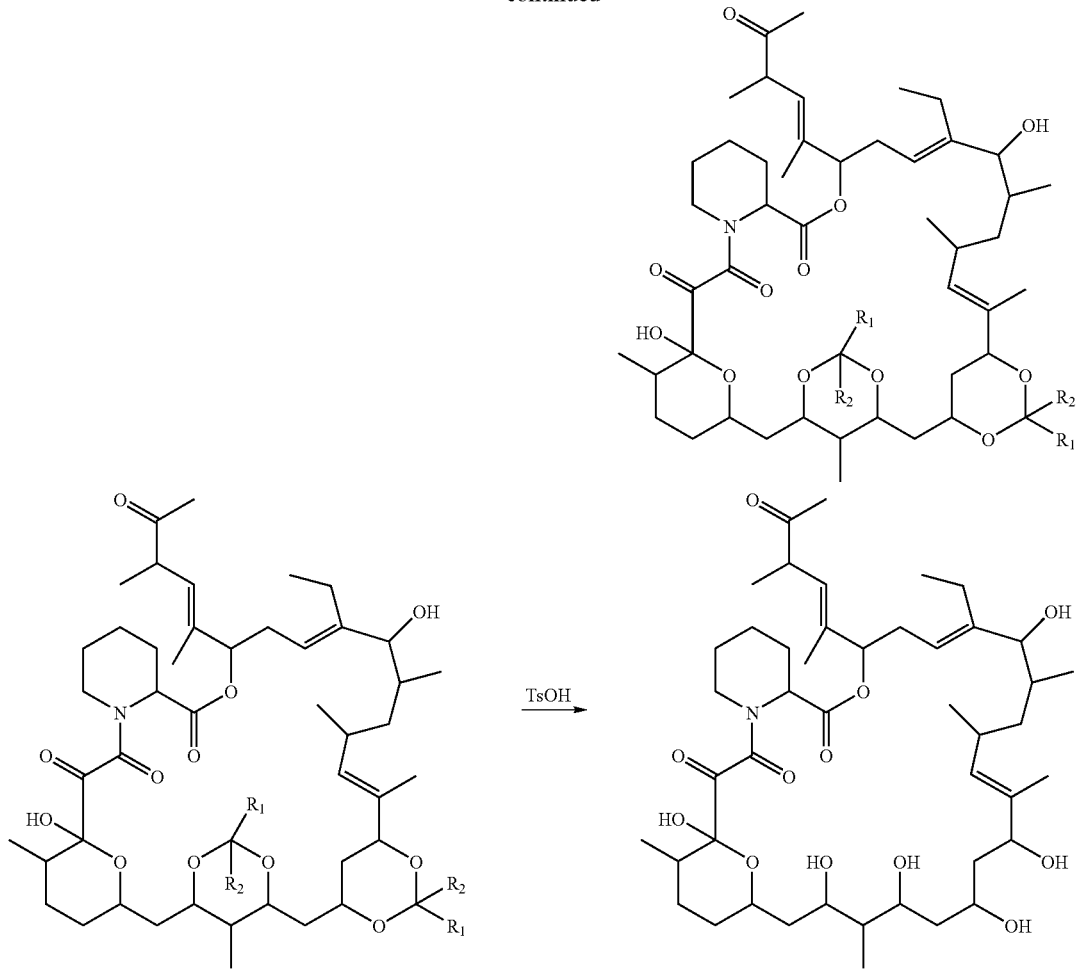

In one aspect, the invention provides the use of the meridamycin compounds produced by the routes described herein and the compounds of the invention in pharmaceutical compositions and methods for a variety of neurological disorders.

The term "preventing neurodegeneration" refers to preventing neuronal cell death by apoptosis, autophagy, or any other mechanism, resulting from a pathological condition including but not limited to a neurodegenerative disease, ischemia, trauma, and any condition resulting from an excess of an excitatory amino acid such as glutamate.

The term "promoting neuroregeneration" refers to inducing in neuronal cell events which include but are not limited to neurite outgrowth or long term potentiation. Neuroprotective agents are useful for the treatment of e.g., neurodegenerative diseases such as Alzheimer's and Parkinson's diseases, neuronal damage following ischemia or trauma, and any other pathological condition in which neuronal damage is implicated.

Although not intending to be limited in its therapeutic applications, it is desirable to use the meridamycin compounds described herein for treatment of conditions of the central nervous system, neurological disorders, and disorders of the peripheral nervous system. Conditions affecting the central nervous system include, but are not limited to, epilepsy, stroke, cerebral ischemia, cerebral palsy, multiple sclerosis, Alper's disease, Parkinson's disease, Alzheimer's disease, Huntington's disease, amyotrophic lateral sclerosis (ALS), dementia with Lewy bodies, Rhett syndrome, neuropathic pain, spinal cord trauma, or traumatic brain injury.

Neurological disorders according to the invention include, but are not limited to, various peripheral neuropathic and neurological disorders related to neurodegeneration including, but not limited to trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, dementia, Alzheimer's disease, Parkinson's disease, and Huntington's chorea.

Specific situations in which neurotrophic therapy is indicated to be warranted include, but are not limited to, central nervous system disorders, Alzheimer's disease, aging, Parkinson's disease, Huntington's disease, multiple sclerosis, amyotrophic lateral sclerosis, traumatic brain injury, spinal cord injury, epilepsy, inflammatory disorders, rheumatoid arthritis, autoimmune diseases, respiratory distress, emphysema, psoriasis, adult respiratory distress syndrome, central nervous system trauma, and stroke.

The meridamycin compounds of this invention are also useful in preventing, treating or inhibiting senile dementias, dementia with Lewy bodies, mild cognitive impairment, Alzheimer's disease, cognitive decline, associated neurodegenerative disorders, as well as providing neuroprotection or cognition enhancement.

The term "subject" or "patient," as used herein, refers to a mammal, which may be a human or a non-human animal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "effective amount" and "therapeutically effective amount," as used herein, refer to the amount of a compound that, when administered to a patient, is effective to at least partially ameliorate a condition from which the patient is suspected to suffer.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual subject being treated. Effective administration of the meridamycin compounds of this invention may be given at monthly, weekly, or daily, or other suitable intervals. For example, a parenteral dose may be delivered on a weekly basis at a dose of about 10 mg to about 1000 mg, about 50 mg to about 500 mg, or about 100 mg to about 250 mg per week. A suitable oral dose may be greater than about 0.1 mg/day. Preferably, administration will be greater than about 10 mg/day, more specifically greater than about 50 mg/day in a single dose or in two or more divided doses. The oral dose generally will not exceed about 1,000 mg/day and more specifically will not exceed about 600 mg/day. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The meridamycin compounds can also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The invention further provides products, including packaging, containing the compounds formulated for delivery. In another aspect, the invention provides kits including, e.g., needles, syringes, and other packaging, for delivery of the compound of the invention. Optionally, such a kit may include directions for administration of the drug, diluent, and or a carrier for mixing of a solid form of a compound of the invention.

The reagents used in the preparation of the compounds of this invention can be either commercially obtained or can be prepared by standard procedures described in the literature.

The following examples are illustrative only and are not intended to be a limitation on the present invention.

EXAMPLES

Example 1

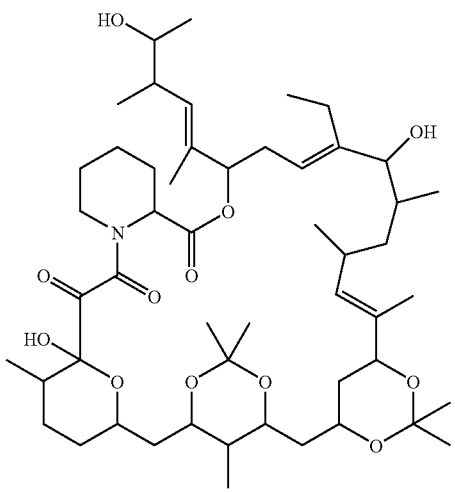

Meridamycin (0.069 g, 0.084 mmol) was dissolved in 5 mL dimethylformamide (DMF). Excess 2,2-dimethoxypropane (0.5 mL, 4 mmol) and a catalytic amount of paratoluenesulfonic acid was added to this DMF solution. The reaction mixture was stirred at 25° C. for 20 hours with magnetic stirring. Chloroform (5 mL) was added to this mixture and the resulting solution was filtered over a small column of basic alumina. The products were then chromatographed via reversed-phase HPLC (column: 250×20 mm YMC ODS-A with 50×20 guard, mobile phase: 50 to 80% acetonitrile:water in 30 minutes, then to 90% acetonitrile in 15 minutes, hold at 90% for an additional 15 minutes) to yield the product (0.028 g, 37% yield, $t_R$=10.6 min, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 901.59153

Theoretical Elemental: $C_{51}H_{83}NO_{12}$

Exact Mass High Resolution Results

| Adduct | Exptl. | Exact | mmu | ppm | RI % |
|---|---|---|---|---|---|
| $[M + Na]^{1+}$ | 924.57895 | 924.58075 | −1.80 | −1.94 | 60.9 |

Example 2

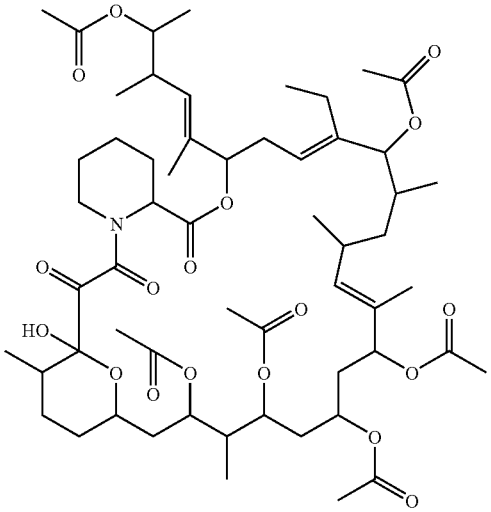

Meridamycin (0.05 g, 0.06 mmol) was dissolved in pyridine (1.0 mL), acetic anhydride (1.0 mL) was added to this solution, and the reaction was stirred for 3 hours. The solvents were removed in vacuo and the products then chromatographed via reversed-phase HPLC (column: 250×10 mm YMC ODS-A, mobile phase: 50 to 95% acetonitrile:water in 20 minutes, hold at 95% for an additional 30 minutes) to yield a fraction that was further chromatographed via reversed-phase HPLC (column: 250×10 mm YMC ODS-A, mobile phase: 80% acetonitrile:water for 30 minutes, then to 90% acetonitrile in 5 minutes, hold at 95% for an additional 10 minutes) to yield the product (0.006 g, 9% yield, $t_R$=8.07 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 1073.59231

Theoretical Elemental: $C_{57}H_{87}NO_{18}$

Exact Mass High Resolution Results

| Adduct | Exptl. | Exact | mmu | ppm | RI % |
|---|---|---|---|---|---|
| $[M + Na]^{1+}$ | 1096.58138 | 1096.58153 | −0.15 | −0.13 | 100.0 |
| $[M + NH_4]^{1+}$ | 1091.62488 | 1091.62613 | −1.25 | −1.15 | 3.9 |
| $[M + K]^{1+}$ | 1112.55633 | 1112.55547 | 0.86 | 0.77 | 1.6 |
| $[M + H + Na]^{2+}$ | 548.79139 | 548.79440 | −3.01 | −5.49 | 1.8 |

Example 3

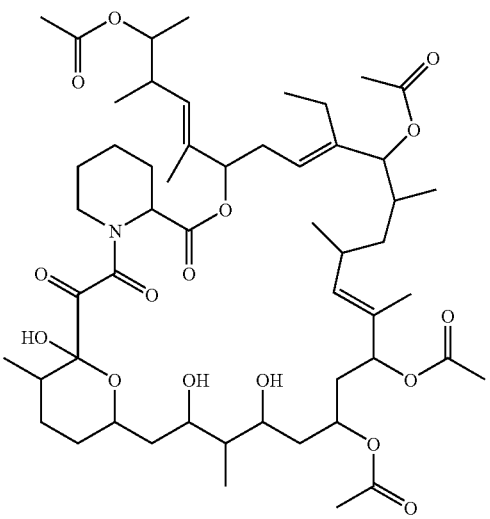

Meridamycin (0.05 g, 0.06 mmol) was dissolved in pyridine (1.0 mL), acetic anhydride (1.0 mL) was added to this pyridine solution, and the reaction was allowed to stir for 3 hours. Solvents were removed in vacuo and the products were then chromatographed via reversed-phase HPLC (column: 250×10 mm YMC ODS-A, mobile phase: 50 to 95% acetonitrile:water in 20 minutes, hold at 95% for an additional 30 minutes) to yield the product (0.008 g, 14% yield, $t_R$=7.40 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 989.57119

Theoretical Elemental: $C_{53}H_{83}NO_{16}$

| Adduct | Exact Mass High Resolution Results | | | | |
|---|---|---|---|---|---|
| | Exptl. | Exact | mmu | ppm | RI % |
| $[M + H]^{1+}$ | 990.57913 | 990.57847 | 0.66 | 0.67 | 2.6 |
| $[M + Na]^{1+}$ | 1012.56339 | 1012.56041 | 2.98 | 2.95 | 37.0 |

Example 4

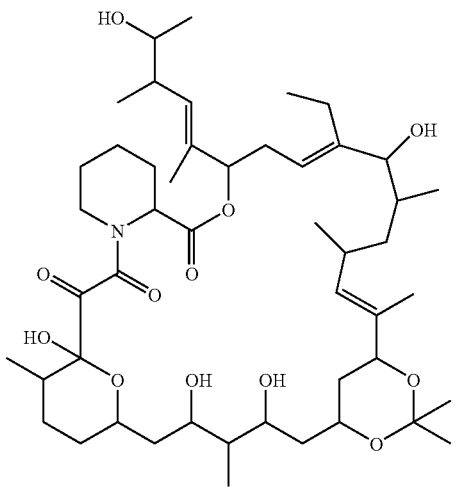

Meridamycin (0.1 g, 0.12 mmol) was dissolved in 2,2-dimethoxypropane (1.50 mL) and a catalytic amount of para-toluenesulfonic acid was added. The reaction mixture was stirred at 25° C. for 16 hours with magnetic stirring. Chloroform (5 mL) was added to the solution and the resulting solution was filtered over a small column of sodium bicarbonate. The products were then chromatographed via reversed-phase HPLC (column: 250×20 mm YMC ODS-A with 50×20 guard, mobile phase: 50 to 80% acetonitrile:water in 30 minutes, then to 90% acetonitrile in 15 minutes, hold at 90% for an additional 15 minutes) to yield the product (0.008 g, 8% yield) $t_R$=10.0 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 861.56023

Theoretical Elemental: $C_{48}H_{79}NO_{12}$

| Adduct | Exact Mass High Resolution Results | | | | |
|---|---|---|---|---|---|
| | Exptl. | Exact | mmu | ppm | RI % |
| $[M + H]^{1+}$ | 862.57146 | 862.56751 | 3.95 | 4.58 | 2.8 |
| $[M + Na]^{1+}$ | 884.55113 | 884.54945 | 1.68 | 1.90 | 29.1 |
| $[M + K]^{1+}$ | 900.52258 | 900.52339 | −0.81 | −0.90 | 1.9 |

Example 5

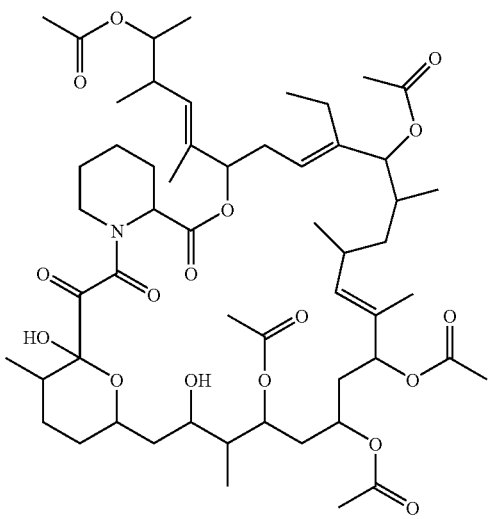

Meridamycin (0.05 g, 0.06 mmol) was dissolved in pyridine (1.0 mL), acetic anhydride (1.0 mL) was added to this pyridine solution, and the reaction was allowed to stir for 3 hours. Solvents were removed in vacuo and the products were then chromatographed via reversed-phase HPLC (column: 250×10 mm YMC ODS-A, mobile phase: 50 to 95% acetonitrile:water in 20 minutes, hold at 95% for an additional 30 minutes) to yield a fraction that was further chromatographed via reversed-phase HPLC (column: 250×10 mm YMC ODS-A, mobile phase: 80% acetonitrile:water for 30 minutes, then to 90% acetonitrile in 5 minutes, hold at 95% for an additional 10 minutes) to yield the product (0.003 g, 5% yield, $t_R$=7.72 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 1031.58175

Theoretical Elemental: $C_{55}H_{85}NO_{17}$

| Exact Mass High Resolution Results | | | | | |
|---|---|---|---|---|---|
| Adduct | Exptl. | Exact | mmu | ppm | RI % |
| $[M + H]^{1+}$ | 1032.58632 | 1032.58903 | −2.71 | −2.62 | 5.6 |
| $[M + Na]^{1+}$ | 1054.57069 | 1054.57097 | −0.28 | −0.26 | 78.8 |
| $[M + H + Na]^{2+}$ | 527.78532 | 527.78912 | −3.80 | −7.20 | 1.6 |

Example 6

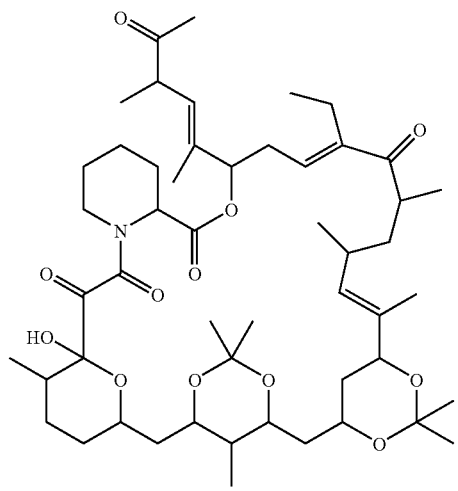

Anhydrous dichloromethane (1.0 mL) was added to a solution of the compound of Example 1 (0.011 g, 0.012 mmol) in a 0.3 M solution of Dess-Martin periodinane in dichloromethane (50 µL). The reaction was stirred under argon for 4 hours, dichloromethane (DCM, 10 mL) was added and the organic layer was washed with saturated sodium carbonate. The organic layer was dried, reduced in vacuo, and chromatographed via reversed-phase HPLC (column: 250×10 mm YMC ODS-A, mobile phase: 50% to 95% acetonitrile:water in 20 minutes, hold at 95% for an additional 30 minutes) to yield the product (0.008 g, 74% yield, $t_R$=10.13 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 897.56023

Theoretical Elemental: $C_{51}H_{79}NO_{12}$

| Exact Mass High Resolution Results | | | | | |
|---|---|---|---|---|---|
| Adduct | Exptl. | Exact | mmu | ppm | RI % |
| $[M + Na]^{1+}$ | 920.54952 | 920.54945 | 0.07 | 0.08 | 53.8 |
| $[M + NH_4]^{1+}$ | 915.59351 | 915.59405 | −0.54 | −0.59 | 9.2 |
| $[M + H + K]^{2+}$ | 468.76132 | 468.76533 | −4.01 | −8.56 | 2.4 |

Example 7

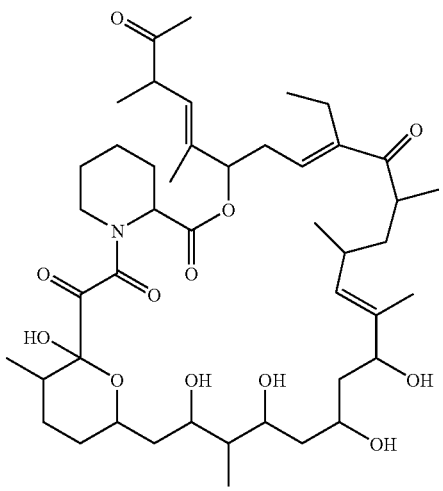

A catalytic amount of paratoluenesulfonic acid was added to a solution of the product of Example 6 (0.005 g, 0.006 mmol) in 2:1 methanol:water (3 mL). The reaction was stirred for 24 hours, the solvents were removed in vacuo, and the products were chromatographed via reversed-phase HPLC (column: 250×10 mm YMC ODS-A, mobile phase: 50% to 80% acetonitrile:water in 10 minutes, hold at 80% for an additional 20 minutes) to yield the product (0.002 g, 41% yield, $t_R$=6.21 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 817.49763

Theoretical Elemental: $C_{45}H_{71}NO_{12}$

Exact Mass High Resolution Results

| Adduct | Exptl. | Exact | mmu | ppm | RI % |
|---|---|---|---|---|---|
| $[M + H]^{1+}$ | 818.50303 | 818.50491 | −1.88 | −2.29 | 41.3 |
| $[M + Na]^{1+}$ | 840.48364 | 840.48685 | −3.21 | −3.82 | 4.3 |
| $[M + K]^{1+}$ | 856.45711 | 856.46079 | −3.68 | −4.29 | 0.2 |
| $[M + CH_3OH + H]^{1+}$ | 850.52978 | 850.53112 | −1.34 | −1.57 | 2.8 |

Example 8

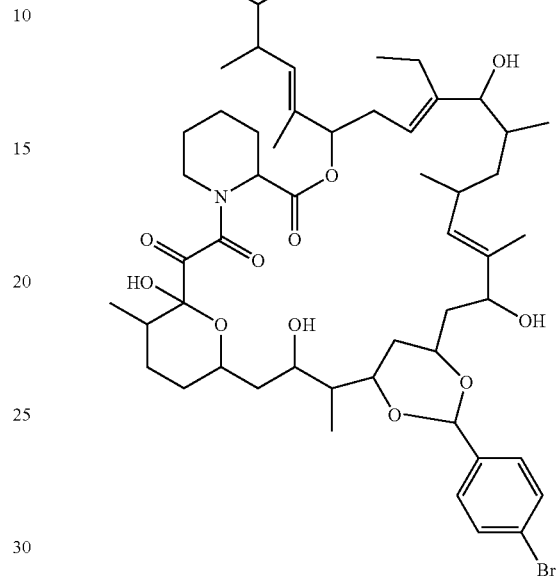

Meridamycin (0.05 g, 0.061 mmol) was dissolved in DMF (2 mL). Excess p-bromobenzaldehyde dimethyl acetal (0.022 mL, 0.128 mmol, 2.1 eq) and a catalytic amount of paratoluenesulfonic acid was added to this DMF solution. The reaction mixture was stirred at 25° C. for 16 hours with magnetic stirring. Chloroform (5 mL) was added to this solution and the resulting solution was filtered over a small column of sodium bicarbonate. The products were then chromatographed via reversed-phase HPLC (column: 250×10 mm YMC ODS-A, mobile phase: 50% to 80% acetonitrile:water in 15 minutes, then to 95% in 35 minutes) to yield the product (0.008 g, 13% yield, $t_R$=7.33 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 987.47074

Theoretical Elemental: $C_{52}H_{78}BrNO_{12}$

Exact Mass High Resolution Results

| Adduct | Exptl. | Exact | mmu | ppm | RI % |
|---|---|---|---|---|---|
| $[M + H]^{1+}$ | 988.47663 | 988.47802 | −1.39 | −1.40 | 1.1 |

Example 9

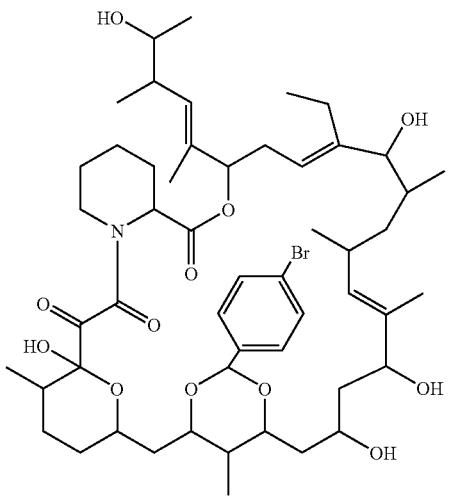

Meridamycin (0.05 g, 0.061 mmol) was dissolved in DMF (2 mL). Excess p-bromobenzaldehyde dimethyl acetal (0.022 mL, 0.128 mmol, 2.1 eq) and a catalytic amount of paratoluenesulfonic acid was added to this DMF solution. The reaction mixture was stirred at 25° C. for 16 hours with magnetic stirring. Chloroform (5 mL) was added to the solution and the resulting solution was filtered over a small column of sodium bicarbonate. The products were then chromatographed via reversed-phase HPLC (column: 250×10 mm YMC ODS-A, mobile phase: 50% to 80% acetonitrile:water in 15 minutes, then to 95% in 35 minutes) to yield the product (0.002 g, 3% yield, $t_R$=6.94 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes).

Theoretical Neutral Mass: 987.47074

Theoretical Elemental: $C_{52}H_{78}BrNO_{12}$

| Exact Mass High Resolution Results | | | | | |
|---|---|---|---|---|---|
| Adduct | Exptl. | Exact | mmu | ppm | RI % |
| $[M + H]^{1+}$ | 988.47973 | 988.47802 | 1.71 | 1.73 | 2.2 |
| $[M + Na]^{1+}$ | 1010.45847 | 1010.45996 | −1.49 | −1.47 | 44.4 |
| $[M + NH_4]^{1+}$ | 1005.50368 | 1005.50456 | −0.88 | −0.88 | 72.7 |

Example 10

Dissociated cortical neuron cultures were prepared as previously described (Pong et al., 2001). Briefly, embryonic day 15 rat fetuses were collected and dissected in ice-cold PBS. Dissected cortices were pooled together and transferred to an enzymatic dissociation medium containing papain. After 30 minutes, the tissue was mechanically triturated with a fire-polished glass Pasteur pipette. Single-cell suspensions in complete media were seeded on poly-L-ornithine and laminin coated 96-well plates. 24 hours later, cultures were treated with various concentrations of compound for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as average neurite length or total neurite length per cell.

The compounds of examples 1-6 were all active in cortical neuron assays with an $EC_{50}$ less than 1 µM.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure:

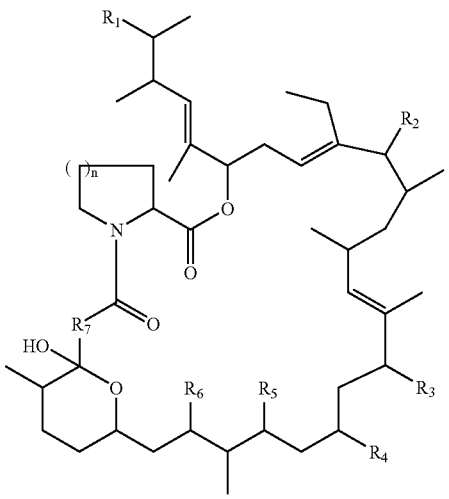

wherein:

$R_1$ and $R_2$ are, independently selected from the group consisting of, OH, oxo, O($C_1$ to $C_6$ alkyl), O(substituted $C_1$ to $C_6$ alkyl), O(acyl), O(aryl), O(substituted aryl), O(heterocyclyl), or O(substituted heterocyclyl);

$R_3$, $R_5$, and $R_6$ are independently are selected from the group consisting of OH, oxo, O($C_1$ to $C_6$ alkyl), O(substituted $C_1$ to $C_6$ alkyl), O(acyl), O(aryl), O(substituted aryl), O(heterocyclyl), and O(substituted heterocyclyl);

$R_4$ is selected from the group consisting of oxo, O($C_1$ to $C_6$ alkyl), O(substituted $C_1$ to $C_6$ alkyl), O(acyl), O(aryl), O(substituted aryl), O(heterocyclyl), and O(substituted heterocyclyl); or $R_3$ and $R_4$ and/or $R_5$ and $R_6$ are joined together to form a structure:

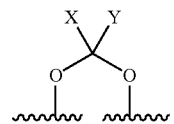

or, R$_4$ and R$_5$ are joined to form a structure:

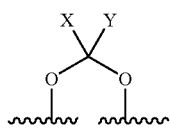

wherein X and Y are independently selected from the group consisting of H, C$_1$ to C$_6$ alkyl, substituted C$_1$ to C$_6$ alkyl, aryl, substituted aryl, heterocyclyl, and substituted heterocyclyl;

wherein the alkyl is substituted with one to three substituents each independently selected from halogen, CN, OH, NO$_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein aryl is a carbocyclic aromatic system having a single ring or multiple aromatic rings fused or linked together forming a conjugated aromatic system and wherein the aryl can be optionally substituted with one to four substituents each independently selected from halogen, CN, OH NO$_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein heterocyclyl is a 4- to 7-membered monocyclic or stable multicyclic heterocyclyl ring, which is saturated, partially saturated, or unsaturated, including carbon atoms and from one to four heteroatoms selected from N, O and S; and may be optionally substituted with one to four substituents each independently selected from halogen, CN, OH NO$_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein the acyl is an RCO group, where R is a C$_1$ to C$_6$ alkyl or substituted C$_1$ to C$_6$ alkyl as defined above and the point of attachment is on the carbon atom R$_7$ is CH$_2$, CHOH, or C=O; and n is 1 or 2;

or a pharmaceutically acceptable salt thereof.

2. The compound according to claim 1, wherein R$_1$ and R$_2$ are independently oxo, OH or O(acyl).

3. The compound according to claim 2, wherein said O(acyl) is OC(O)CH$_3$.

4. The compound according to claim 1, wherein R$_3$ and R$_4$ or R$_4$ and R$_5$ are joined, wherein X and Y are CH$_3$.

5. The compound according to claim 1, wherein R$_7$ is C(O).

6. The compound according to claim 1 which is selected from the group consisting of:

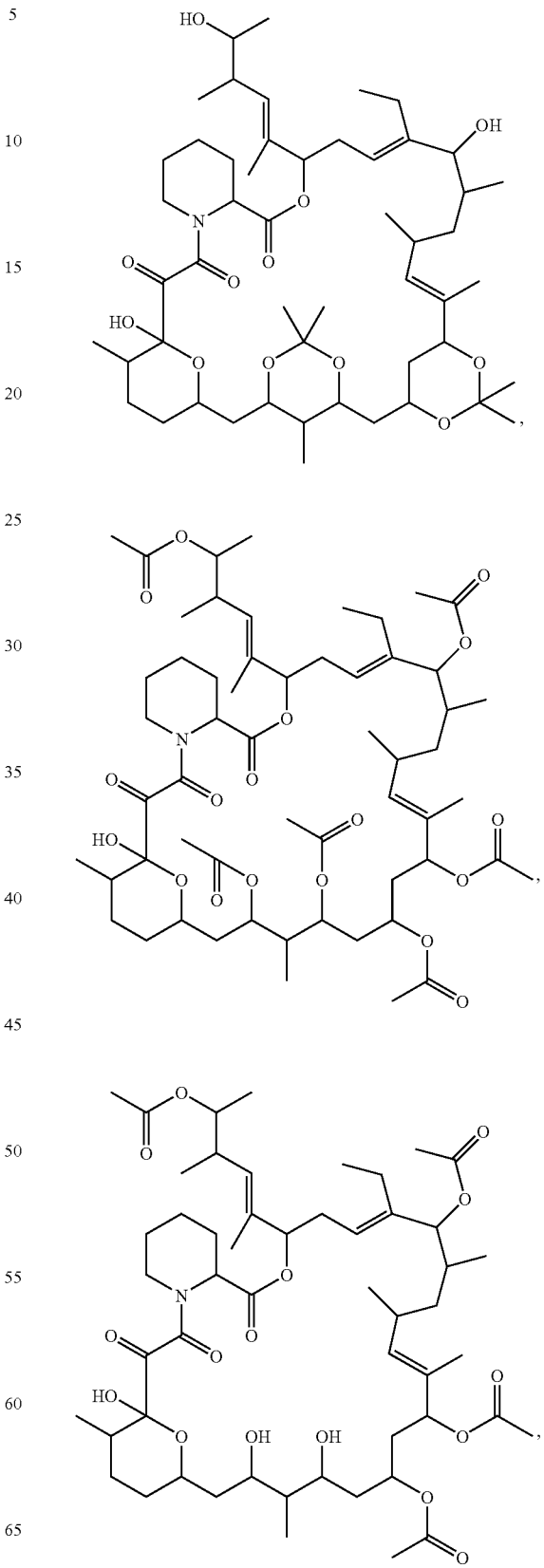

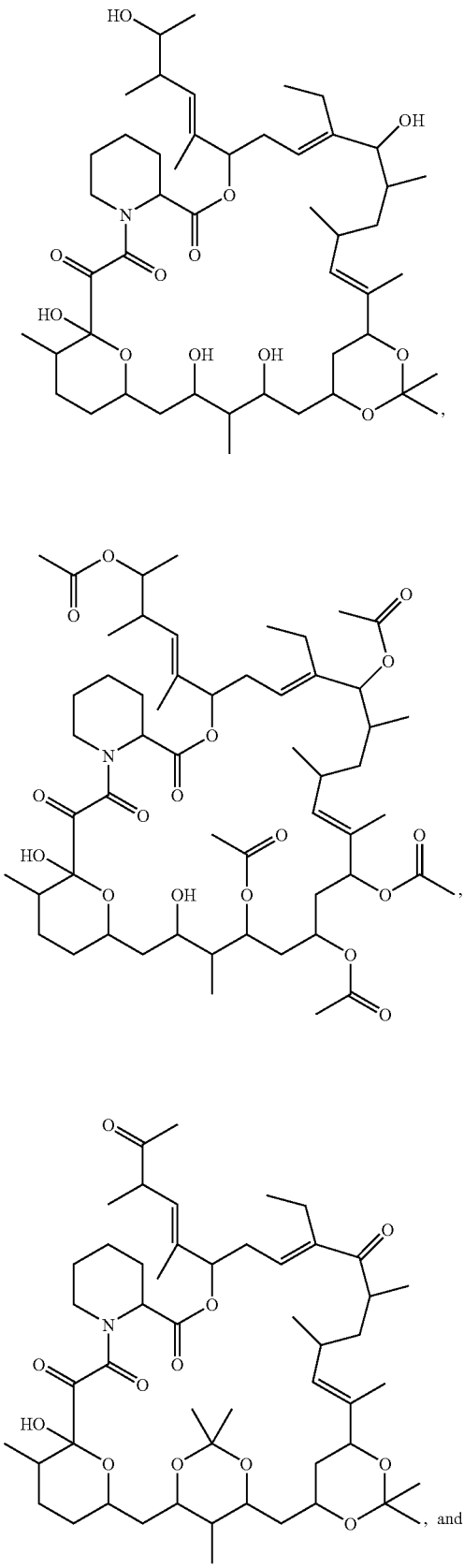

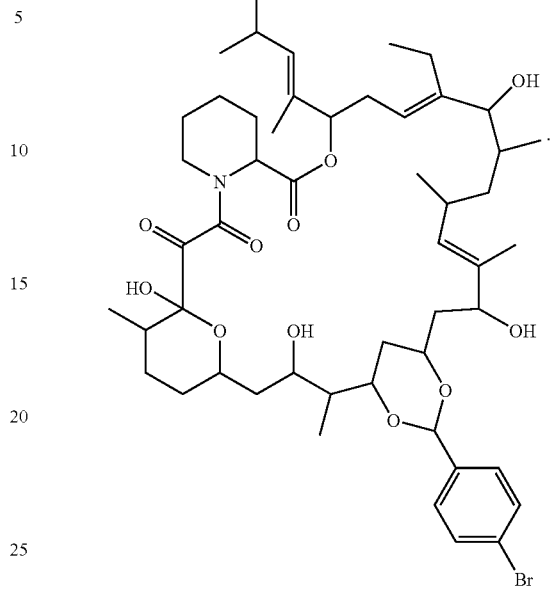

7. The compound according to claim 1, wherein $R_1$ and $R_2$ are OH; $R_3$ and $R_4$ are joined; $R_5$ and $R_6$ are joined; $R_7$ is C(O); and n is 2.

8. The compound according to claim 1, wherein $R_1$, $R_2$, $R_3$, $R_4$, $R_5$, and $R_6$ are OC(O)CH$_3$; $R_7$ is C(O); and n is 2.

9. The compound according to claim 1, wherein $R_1$, $R_2$, $R_3$, and $R_4$ are OC(O)CH$_3$; $R_4$ and $R_5$ are OH; $R_7$ is C(O); and n is 2.

10. The compound according to claim 1, wherein $R_1$, $R_2$, $R_5$, and $R_6$ are OH; $R_3$ and $R_4$ are joined; $R_7$ is C(O); and n is 2.

11. The compound according to claim 1, wherein $R_1$, $R_2$, $R_3$, $R_4$, and $R_5$ are OC(O)CH$_3$; $R_6$ is OH; $R_7$ is C(O); and n is 2.

12. The compound according to claim 1, wherein $R_1$ and $R_2$ are oxo; $R_3$ and $R_4$ and $R_5$ and $R_6$ are joined; $R_7$ is C(O); and n is 2.

13. The compound according to claim 1, wherein $R_1$ and $R_2$ are oxo; $R_3$, $R_4$, $R_5$, and $R_6$ are OH; $R_7$ is C(O); and n is 2.

14. The compound according to claim 1, wherein $R_1$, $R_2$, $R_3$, and $R_6$ are OH; $R_7$ is C(O); n is 2; and $R_4$ and $R_5$ are taken together to form a ring of the structure:

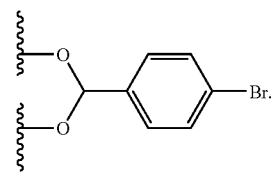

15. The compound according to claim 1, wherein $R_1$, $R_2$, $R_3$ and $R_4$ are OH; $R_7$ is C(O); n is 2; and $R_5$ and $R_6$ are taken together to form a ring of the structure:

[Structure: acetal group with 4-bromophenyl]

16. A compound as claimed in claim 1, wherein $R_1$ and $R_2$ are, independently, OH, oxo, or O(acyl);

$R_3$, $R_5$, and $R_6$ are independently selected from the group consisting of OH and O(acyl);

$R_4$ is O(acyl), or $R_3$ and $R_4$; $R_4$ and $R_5$; $R_5$ and $R_6$; or a combination thereof are joined to form a structure:

[Structure: cyclic acetal with X and Y substituents]

wherein X and Y are independently selected from the group consisting of H and $C_1$ to $C_6$ alkyl;

$R_7$ is C=O; and n is 2;

or a pharmaceutically acceptable salt thereof.

17. A pharmaceutical composition comprising a compound according to claim 1 and one or more pharmaceutically acceptable carriers, excipients, or diluents.

18. A method of preparing a compound of the structure:

[Macrocyclic structure with R_1–R_7 and n]

wherein:

$R_1$, $R_2$, $R_3$, $R_4$, $R_5$, and $R_6$ are, independently, O($C_1$ to $C_6$ alkyl) or O(substituted $C_1$ to $C_6$ alkyl);

$R_7$ is $CH_2$, CHOH, or C=O; and n is 1 or 2;

or a pharmaceutically acceptable salt thereof wherein said method comprises reacting meridamycin with an alkylating agent or alkyl anhydride.

19. The method according to claim 18, wherein said alkylating agent is an alkyl halide, alkyl triflate, or alkyl mesylate.

20. The method according to claim 18, wherein said alkyl anhydride is acetic anhydride.

21. A method of preparing a compound of the structure:

[Macrocyclic structure with R_1–R_7 and n]

wherein:

$R_1$ and $R_2$ are OH;

$R_3$ and $R_4$ and/or $R_4$ and $R_5$, or $R_5$ and $R_6$, are joined to form a structure:

[Structure: cyclic acetal with X and Y substituents]

X and Y are independently selected from the group consisting of H, $C_1$ to $C_6$ alkyl, substituted $C_1$ to $C_6$ alkyl, aryl, substituted aryl, heterocyclyl, and substituted heterocyclyl;

$R_7$ is $CH_2$, CHOH, or C=O; and n is 1 or 2;

or a pharmaceutically acceptable salt thereof wherein, said method comprises reacting meridamycin with a dialkoxyalkane in the presence of an acid catalyst.

22. The method according to claim 21, wherein said dialkoxyalkane is 2,2-dimethoxypropane.

23. The method according to claim 21, wherein said acid catalyst is paratoluenesulfonic acid.

24. A method of preparing a compound of the structure:

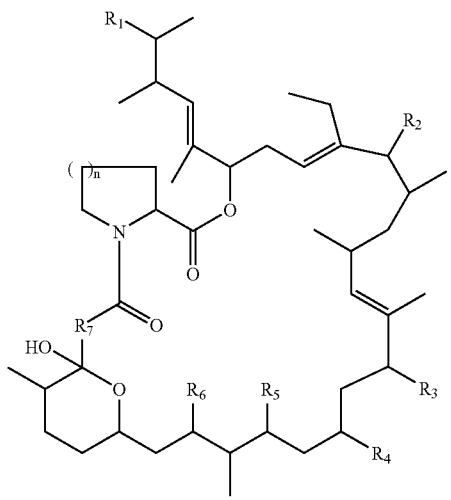

wherein:

$R_1$ and $R_2$ are oxo;

$R_3$ and $R_4$ and/or $R_4$ and $R_5$, or $R_5$ and $R_6$, are joined to form a structure:

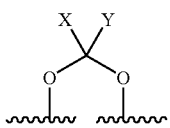

wherein X and Y are independently selected from the group consisting of H, $C_1$ to $C_6$ alkyl, substituted $C_1$ to $C_6$ alkyl, aryl, substituted aryl, heterocyclyl, and substituted heterocyclyl;

wherein the alkyl can be substituted with one to three substituents each independently selected from halogen, CN, OH, $NO_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein aryl is a carbocyclic aromatic system having a single ring or multiple aromatic rings fused or linked together forming a conjugated aromatic system and wherein the aryl can be optionally substituted with one to four substituents each independently selected from halogen, CN, OH $NO_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein heterocyclyl is a 4- to 7-membered monocyclic or stable multicyclic heterocyclyl ring, which is saturated, partially saturated, or unsaturated, including carbon atoms and from one to four heteroatoms selected from N, O and S; and may be optionally substituted with one to four substituents each independently selected from halogen, CN, OH $NO_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

$R_7$ is $CH_2$, CHOH, or C=O; and n is 1 or 2;

or a pharmaceutically acceptable salt thereof wherein said method comprises reacting the compound prepared according to claim 21 with the Dess-Martin periodinane reagent.

25. A method of preparing a compound of the structure:

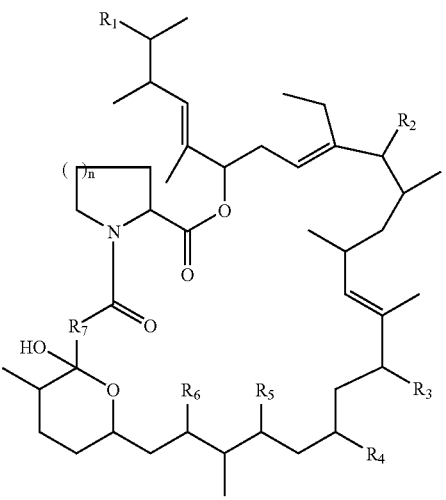

wherein:

$R_1$ is oxo;

$R_2$ is OH;

$R_3$ and $R_4$ and/or $R_4$ and $R_5$, or $R_5$ and $R_6$, are joined to form a structure:

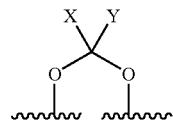

X and Y are independently selected from the group consisting of H, $C_1$ to $C_6$ alkyl, substituted $C_1$ to $C_6$ alkyl, aryl, substituted aryl, heterocyclyl, and substituted heterocyclyl;

wherein the alkyl is substituted with one to three substituents each independently selected from halogen, CN, OH, $NO_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein aryl is a carbocyclic aromatic system having a single ring or multiple aromatic rings fused or linked together forming a conjugated aromatic system and wherein the aryl can be optionally substituted with one to four substituents each independently selected from halogen, CN, OH $NO_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

wherein heterocyclyl is a 4- to 7-membered monocyclic or stable multicyclic heterocyclyl ring, which is saturated, partially saturated, or unsaturated, including carbon atoms and from one to four heteroatoms selected from N, O and S; and may be optionally substituted with one to four substituents each independently selected from halogen, CN, OH NO$_2$, amino, aryl, heterocyclyl, substituted aryl, substituted heterocyclyl, alkoxy, substituted alkoxy, aryloxy, substituted aryloxy, alkylcarbonyl, alkylcarboxy, alkylamino, and arylthio;

R$_7$ is CH$_2$, CHOH, or C=O; and n is 1 or 2;

or a pharmaceutically acceptable salt thereof;

wherein said method comprises treating the compound prepared according to claim 21 with tetrapropylammonium ruthenate and N-morpholine oxide.

26. A method for preparing a compound of the structure:

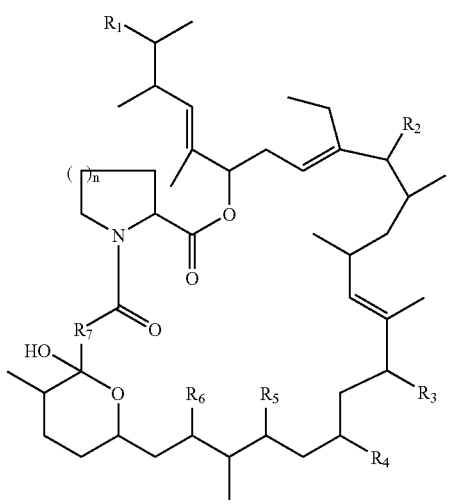

wherein:

R$_1$ is oxo;

R$_2$ is OH;

R$_3$, R$_5$, and R$_6$ are OH;

R$_4$ is selected from oxo, O(C$_1$ to C$_6$ alkyl), O(substituted C$_1$ to C$_6$ alkyl), O(acyl), O(aryl), O(substituted aryl), O(heterocyclyl), and O(substituted heterocyclyl)

R$_7$ is CH$_2$, CHOH, or C=O; and n is 1 or 2;

or a pharmaceutically acceptable salt thereof wherein said method comprises reacting the product of claim 25 with a weak acid.

27. The method according to claim 26, wherein said weak acid is paratoluenesulfonic acid.

28. A compound selected from:

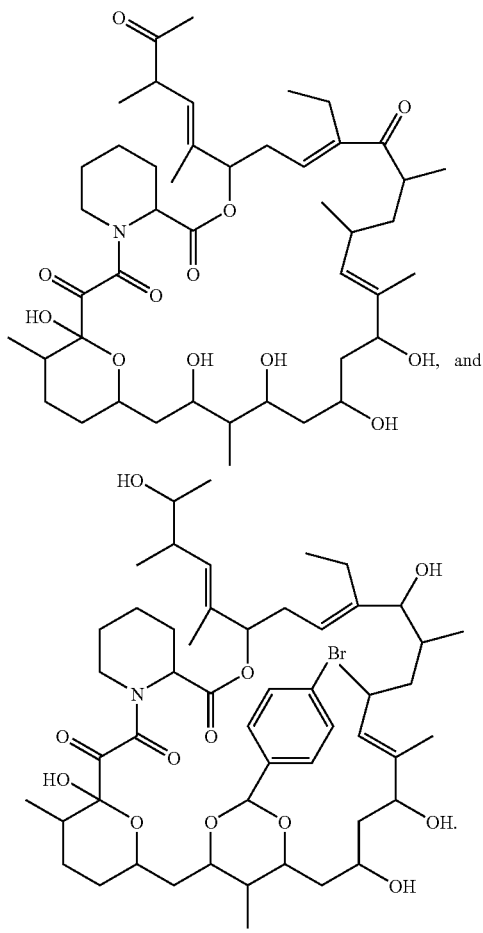

29. A pharmaceutical composition comprising a compound according to claim 28 and one or more pharmaceutically acceptable carriers, excipients, or diluents.

* * * * *